(12) United States Patent
Nevo (10) Patent No.: US 6,224,553 B1
(45) Date of Patent: May 1, 2001

(54) METHOD AND APPARATUS FOR THE ASSESSMENT AND DISPLAY OF VARIABILITY IN MECHANICAL ACTIVITY OF THE HEART, AND ENHANCEMENT OF ULTRASOUND CONTRAST IMAGING BY VARIABILITY ANALYSIS

(75) Inventor: Erez Nevo, Natania (IL)

(73) Assignee: Robin Medical, Inc., Baltimore, MD (US)

( * ) Notice: Subject to any disclaimer, the term of this patent is extended or adjusted under 35 U.S.C. 154(b) by 0 days.

(21) Appl. No.: 09/380,509
(22) PCT Filed: Mar. 9, 1998
(86) PCT No.: PCT/US98/03932
§ 371 Date: Sep. 3, 1999
§ 102(e) Date: Sep. 3, 1999
(87) PCT Pub. No.: WO98/40014
PCT Pub. Date: Sep. 17, 1998

Related U.S. Application Data (60) Provisional application No. 60/040,258, filed on Mar. 10, 1997, and provisional application No. 60/056,536, filed on Aug. 19, 1997.

(51) Int. Cl.$^7$ .................................................. A61B 8/00
(52) U.S. Cl. ............................................................ 600/437
(58) Field of Search .................................. 600/437, 447, 600/443, 449, 438, 448; 73/626

(56) References Cited

U.S. PATENT DOCUMENTS

| 4,161,121 | * | 7/1979 | Zitelli et al. | 600/437 |
| 4,241,610 | * | 12/1980 | Anderson | 73/626 |
| 5,902,242 | * | 5/1999 | Ustuner et al. | 600/443 |

* cited by examiner

Primary Examiner—Brian L. Casler
Assistant Examiner—Maulin Patel (57) ABSTRACT

This invention is a method of evaluating the mechanical variability of the heart activity by assessment of the variability of cardiologic echo Doppler images, and of enhancing contrast ultrasound imaging by variability imaging of two-dimensional echo images through the application of finite memory, ECG gated or ungated processing of the acquired images. For cardiac imaging and blood perfusion studies of non-cardiac structures, the acquired images are time-gated by the cardiac cycle to account for cardiac deformation due to contraction, relaxing and filling. To compare blood perfusion characteristics in normal tissue and abnormal tissue, a non-gated version, or gating to another physiologic cycle (e.g. breathing) can be used. The gated scans are either recursive processed in real time or are recorded and processed off-line to get estimation of the mean image and the variability of the image. The resulting images of the mean and variance are displayed for user interpretation.

40 Claims, 5 Drawing Sheets

METHOD AND APPARATUS FOR THE ASSESSMENT AND DISPLAY OF VARIABILITY IN MECHANICAL ACTIVITY OF THE HEART, AND ENHANCEMENT OF ULTRASOUND CONTRAST IMAGING BY VARIABILITY ANALYSIS

This application claims benefit to U.S. provisional application Ser. No. 60/040,258 filed Mar. 10, 1997 and application Ser. No. 60/056,536 filed Aug. 19, 1997.

BACKGROUND OF THE INVENTION

Mechanical Variability of the Heart

Various cardiovascular variables demonstrate beat-to-beat variability around a constant or slowly changing mean value: Heart-rate variability (the beat-to-beat variability of cardiac cycle length, Woo et al., "Patterns of beat-to-beat heart rate variability in advanced heart failure". American Heart Journal. 123(3):704–10, 1992), blood pressure variability (Parati et al, "Neural cardiovascular regulation and 24-hour blood pressure and heart rate variability", Annals of the New York Academy of Sciences. 783:47–63, 1996), QT-interval variability and dispersion, the temporal and spatial variability of myocardial relaxation (Barr et al., "QT dispersion and sudden unexpected death in chronic heart failure", The Lancet. vol. 343:327–329, 1994), T-wave alternans (Verrier and Nearing, "Electrophysiologic basis for T-wave alternans as an index of vulnerability to ventricular fibrillation", Journal of Cardiovascular Electrophysiology, 5:445–461, 1994). Most of these indices are derived from the ECG and thus represent variabilities of electrical activation and relaxation mechanisms, either directly due to inherent factors or indirectly induced by other mechanisms (e.g. the effect of breathing on heart rate and blood pressure variabilities). Since mechanical variability is associated with electrical variability through electrical-mechanical coupling, partial information about mechanical variability can be gained from the electrical variability. However, there is no methodology and apparatus for direct evaluation of mechanical variability of myocardial activity, namely variability in the contraction, relaxation and filling phases of the heart cycle.

The aforementioned variability indices were demonstrated to be clinically useful in the evaluation of heart failure (Woo et ale. "Patterns of beat-to-beat heart rate variability in advanced heart failure", American Heart Journal. 1223(3):704–10, 1992), risk of sudden-death (American College of Cardiology Cardiovascular Technology Assessment Committee, "Heart rate variability for risk stratification of life-threatening arrhythmias", Journal of the American College of Cardiology, 22(3):948–50, 1993; Barr et al., "QT dispersion and sudden unexpected death in chronic heart failure", The Lancet, 343:327–329, 1994), vulnerability to arrhythmia (e.g. Verrier and Nearing, "Electrophysiologic basis for T-wave alternans as an index of vulnerabilily to ventricular fibrillation", Journal of Cardiovascular Electrophysiology, 5:445–461, 1994). These methodologies do not directly evaluate the mechanical variability of the heart and cannot provide cardiac regional variability. For many patients with regional myocardial injuries (like acute myocardial infarct), these methodologies may not be sensitive enough to contribute to the diagnosis. Accordingly, there is a need for a non-invasive methodology which can directly measure mechanical variability both globally (for the whole heart) and locally, and thus increase the sensitivity and specificity of correct diagnosis of various cardiac diseases.

Ultrasound Contrast Imaging

Ultrasound contrast imaging, the use of contrast agents to enhance ultrasound-derived images, is clinically useful to enable better evaluation of the scanned structures (e.g. enhancement of cardiac chambers) or to enable quantitative assessment of blood perfusion to various organs. Compared with other contrast-enhanced imaging modalities, like CT and MRI, ultrasonic imaging is simpler, faster and less expensive (Thomas J D, Griffin B P, White R D, "Cardiac imaging techniques: which, when, and why", Cleveland Clinic Journal of Medicine, 63(4):213–20, 1996).

Although currently available contrast agents significantly enhance ultrasound imaging and enable assessment of blood perfusion to various organs (Porter T R, Li S, Kricsfeld D, Armbruster R W, "Detection of myocardial perfusion in multiple echocardiographic windows with one intravenous injection of micro bubbles using transient response second harmonic imaging", Journal of the American College of Cardiology, 29(4):791–9, 1997), there is a need to further enhance the ultrasound-derived images in order to achieve efficacy comparable to other imaging modalities. This can be achieved by development of better contrast agents, or by enhancing the contrast agent effect through specifically designed ultrasound systems or ultrasound image modalities. The second-harmonic and power harmonic (Porter T, Xie F, Kricsfeld D, Armbruster R W, "Improved myocardial contrast with second harmonic transient ultrasound response imaging in humans using intravenous perfluorocarbon-exposed sonicated dextrose albumin", Journal of the American College of Cardiology, 27(6):1497–501, 1996) are examples of contrast enhancement through changes in the ultrasound scanning technology. Yet another potential approach is to achieve the enhancement through processing of the ultrasound-derived images. Kaul and colleagues have used image subtraction methodology to enhance the contrast effect for myocardial perfusion studies (Kaul S, "Myocardial Contrast Echo", Current Problems in Cardiology, 22(11):572–582, 1997). They have averaged several pre-contrast images and several with-contrast images and then subtracted the two averages to achieve an image composed mainly of the change between the pre-contrast and the contrast states. However, due to the random nature of the echoes from the bubbles the averaging process result in attenuation of the contrast effect.

Objects of the Invention

It is therefore an object of the present invention to provide a method and apparatus for the evaluation of myocardial variability through the measurement of the variability of ultrasound-derived images of the heart.

It is another object of the present invention to present the variability of the image of the heart using easily interpreted display for various clinical applications.

It is another object of the present invention to provide a method and apparatus for the enhancement of contrast ultrasound imaging through variability analysis of the contrast-echo images, either in real-time or by off-line analysis.

It is another object of the present invention to enhance blood-pool images (e.g. heart chambers) through variability analysis of the contrast-enhanced images.

Yet another object of the present invention is to enable quantitative assessment of the dynamics of blood perfusion to various organs and tissues based on variability analysis of the contrast-enhanced images.

Still another object of the present invention is to develop a methodology to present the enhanced contrast-echo image to the operator through either real-time or off-line image display.

In general, variability of an imaged object can be assessed by acquisition of multiple images and evaluation of the variation of the acquired images of the object. When the imaged object is the beating heart, or when one is interested in blood perfusion or flow, a difficulty arises due to the dynamic change of the cardiac shape or the pulsatile nature of blood flow. This can be overcome by comparing images acquired during the same phase of heart activity, which can be achieved by gating the images to a specific event which marks a specific phase at each cycle. The use of the R-wave of the ECG for gating the scanned images of cardiologic echo-Doppler system to achieve image enhancement by averaging the gated images was disclosed in a co-pending provisional patent application Ser. No. 60/018,466 of Nevo et al., filed May 28, 1996, now PCT/US97/09455, published Dec. 4, 1997 as WO 97/45058.

The current invention uses the gated images to evaluate the variability of the mechanical activity of the beating heart. The heart cycle is divided into "m" equal sequences, which are timed with respect to a fiducial point on the QRS complex, like the tip of the R-wave. Gating the acquired images of the heart eliminates the temporal variation of the image due to functional movement of heart structures (during contraction, relaxation and filling of the cardiac chambers). The gated images, namely images with the same time delay in reference to the R-wave, represent the heart during the same phase of the cardiac cycle, and should be similar if there is no variability in the heart function. Actually, the images are not identical and differ to some extent from each other. The level of variation of each image, compared with the mean (the average of all images with the same time delay), represents the mechanical variability of the heart at the specific time point during the heart cycle. This information can be displayed by various methodologies, for example by a color coding scheme which assigns a different color to each level of variability. Ideally, the variability is estimated in real-time and displayed to the operator when the image is acquired. This approach can be applied with all modes of commercial echo-Doppler systems, namely 2-dimensional mode, m-mode, Doppler, color-Doppler, tissue-Doppler and 3-dimensional imaging.

The micro-bubbles of the contrast agents create highly variable echoes. Echoes coming from the same spatial point but at different times (e.g. once during each heart cycle) are variable and result in a variable ultrasound image (i.e. different gray level of a specific pixel at different times). In contrast, structural elements like myocardium generate less variable echoes and result in more stable gray level of the ultrasound image.

Similarly, R-wave gating can be used to enhance the 2-dimensional image of the heart or the Doppler image of blood flow during contrast ultrasound imaging.

Unlike cardiac variability imaging, which requires gating to the R-wave to prevent image smearing, variability of non-cardiac structures and tissues can be assessed without gating. This may be useful when one expects different levels of pulsatility of blood perfusion in a certain scanned area. For example, it is well documented that blood vessels in tumors of certain tissue, are different than blood vessels in the normal tissues. The different mechanical and anatomical properties of the blood vessels result in different level of blood vessel pulsations induced by the inflowing blood. This may result in different levels of variability of the tumor area compared with the normal tissue, and may be of use to delineate abnormal from normal tissue by contrast ultrasound imaging.

Another application of variability analysis of consecutive images is to quantify the dynamics of transient appearance ("first pass") or disappearance ("wash-out") of the contrast agent. The current approach of video densitometry is based on assessment of the gray level of the pixels in a specific region of interest (ROI) either at a specific phase of the heart contraction or at consecutive frames, and the generation of "activity curve" which provides the temporal change of gray level of these pixels. The current invention enables real-time measurement of the dynamic of blood perfusion across the whole 2-D image and for all phases of cardiac contraction through automatic variability analysis. It thus significantly enhances the current available technology for quantitative assessment of tissue blood perfusion.

The current invention uses either real-time or off-line image variability analysis to enhance the effect of contrast agents during ultrasound scan of specific organ or tissue. For enhancement of cardiac blood-pool (i.e. heart chambers) and myocardial perfusion, or to assess the pulsatile perfusion to any non-cardiac structure, the heart cycle is divided into "m" equal sequences, which are timed with respect to a fiducial point on the QRS complex, like the tip of the R-wave. Gating the acquired images of the heart prevents smearing of the image by the elimination of the temporal variation of the image due to functional movement of heart structures. Similarly, additional gating to breathing cycle may eliminate image smearing due to breathing-induced movements of the scanned structures.

Quantification of blood perfusion to myocardium or other tissues can be achieved by either imaging of a transient appearance of the contrast agent ("first pass") or by steady-state, equilibrium imaging. Initiating the variability assessment with contrast-free image, and continuing through the appearance of the contrast agent until it achieves a full contrast effect, results in high variability of regions having high content of blood. Yet first pass imaging is available once for every injection of the contrast agent, and steady state assessment is required as well. The high temporal variation of the contrast agents, which stem from the random appearance of the micro-bubbles at different times, compared with the relatively low variability of structural elements (e.g. myocardium), results in improved delineation between anatomic structures or tissues with poorly perfused areas, compared with echoes from blood pool regions or well-perfused regions.

The enhanced images can be displayed by various methodologies. The basic display is with grey-level images, were the processed images (the variability image or the ratio between the variability image and the average image) benefit from the improved contrast between the structural components (e.g. myocardium) and the contrast-enhanced regions (e.g. blood pools). To enhance the discrimination between these regions the display can use a color coding scheme which assigns a different color to each level of variability, or contour plots overlayed over the raw image or over the averaged image. Ideally, the variability is estimated in real-time and displayed to the operator when the image is acquired. However, the analysis and display can be done from video or digitally recorded studies. The proposed methodology can be applied with all modes of commercial echo-Doppler systems which are used with contrast imaging, namely 2-dimensional (B-mode) by either fundamental frequency, second harmonic or power harmonic imaging, flow imaging by Doppler and color Doppler mode, and m-mode.

The invention also discloses apparatus to enable the application of the described method either as an external add-on device for commercial echo-Doppler systems or as a built-in module installed within the echo-Doppler systems.

The apparatus comprises an interface to acquire the image from the echo-Doppler system, an interface to obtain the gating signal, memory modules to save the gated images, user interface to control parameters of the algorithm, microprocessor for mathematical processing of the images, and an interface to present the averaged image and its variability.

DETAILED DESCRIPTION OF THE PREFERRED EMBODIMENT

Figure 1:
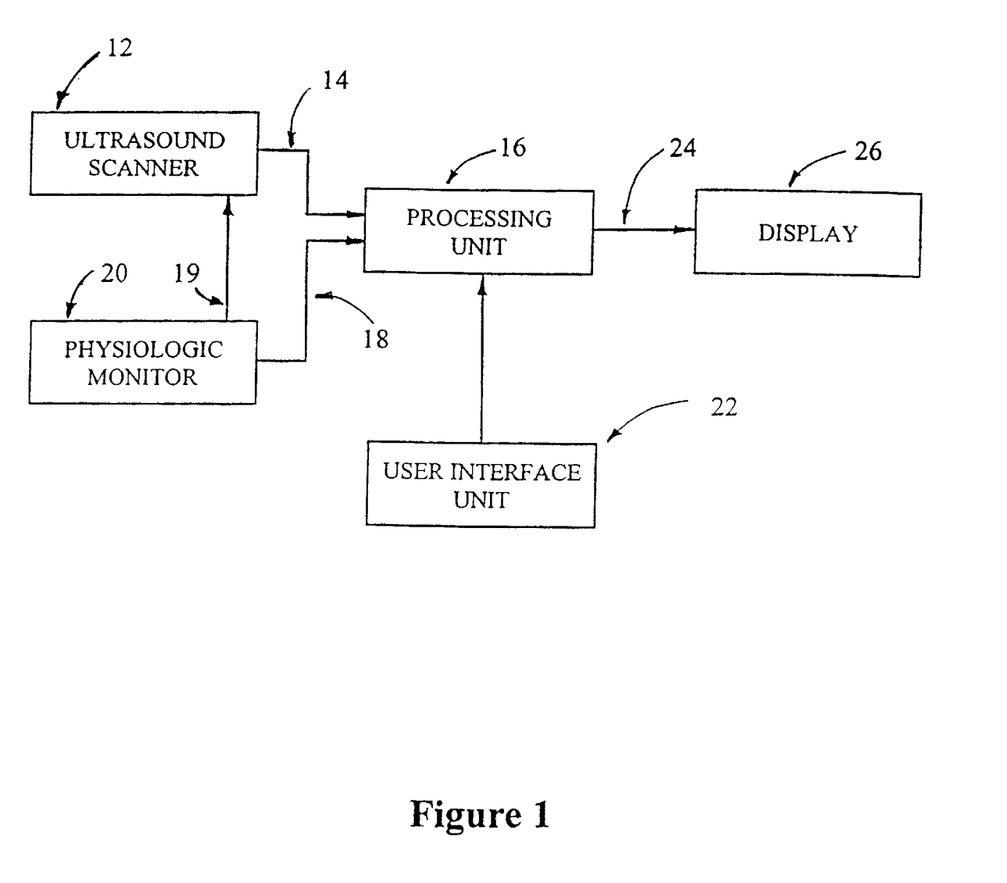
FIG. 1 is a schematic diagram of the proposed system according with the present invention.

Referring now to FIG. 1, there is illustrated an ultrasonic echo-Doppler scanner 12 which provides raw scanned images 14 of the heart to a processing unit 16, where they are processed and stored. A physiologic signal 18, such as the R-wave of the ECG or baseline modulation of the ECG signal which tracks breathing cycle, is provided by physiologic monitor 20 to the processing unit 16. Optionally, a similar or identical physiologic signal 19 is supplied to the scanner 12 to control the timing of the scanning. Signal 18 provides a timing-gating signal through which the ultrasonic image 14 is received by processing unit 16, i.e., each image is tagged with a specific time in cycle with reference to a physiological reference point. Moreover, to achieve better performance, the scanner can be "slaved" to the physiologic monitor through signal 19 so that once the trigger event occurs, the scanner starts a new scan (even if the current scan is not completed). A total of "m" tagged images are created if the cardiac cycle is divided into "m" sequences.

Various user controls, employing the parameters of either recursive algorithm for real-time analysis or batch algorithm for off-line analysis, are set by the user through a user interface unit 22. The scanned raw images 14 are processed, preferably in real-time, but alternatively post-acquisition to provide a variance image 24 which is provided to display 26 for viewing. The "m" processed variance images corresponding to the "m" images, are displayed on display 26 with their corresponding times in reference to the physiological reference point.

Figure 2:
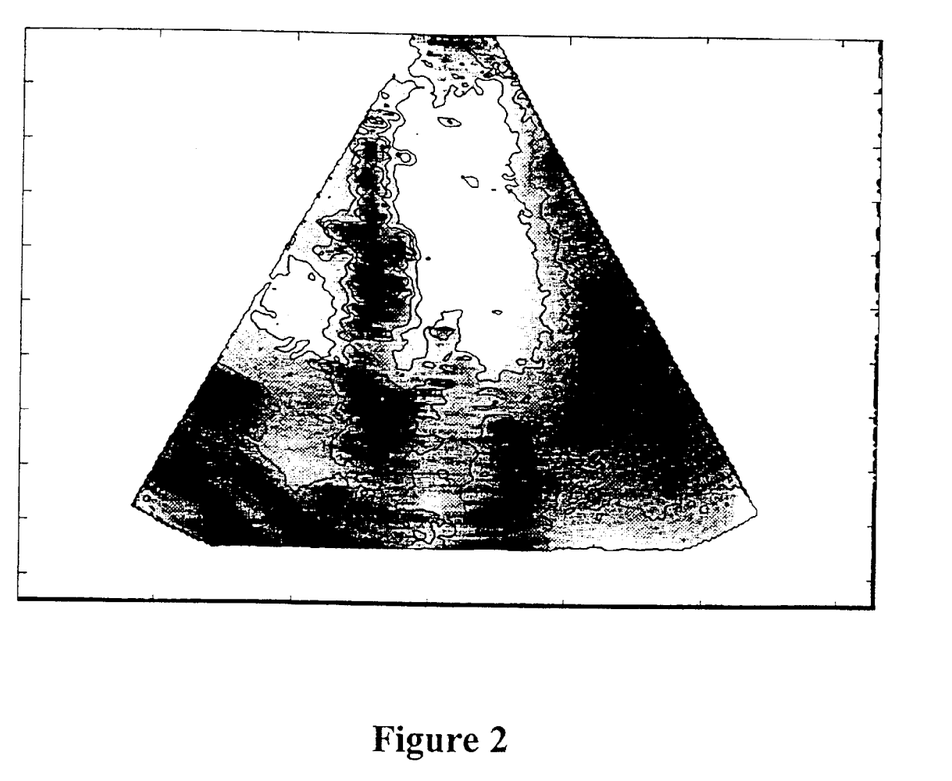
FIG. 2 is an example of image variability presented as superimposed contour lines on a gray level averaged image of the heart (4 chambers view) at end-diastole.

Since the variance changes with time and location, and the variance should be referred to the underlying anatomy of the heart, the preferred presentation methodology includes dynamic presentation of the averaged images (e.g. infinite "cine-loop" of the whole cardiac cycle for off-line presentation or real-time display of the recursively estimated mean image) and an overlay presentation of the variance at each pixel using a color-code scheme (the color changes with the level of the variance) or a contour plot which presents the level of the variance like a topographic map (FIG. 2). The color-code scheme assigns a different color to different levels of the variability, for example, high level of variability is coded as red colors, mid levels are yellow, and low levels are blue.

Other images which are derived by the present approach may be used. For example, the image of the ratio between the standard deviation image (the square root of the variability image) and the average image has the advantage of spatial normalization of image brightness, which can compensate for lower brightness due to attenuated echoes from specific area. This is particularly important with contrast imaging due to shadowing of deeper regions by more proximal (in reference to the transducer) blood pool containing contrast agent.

Figure 3:
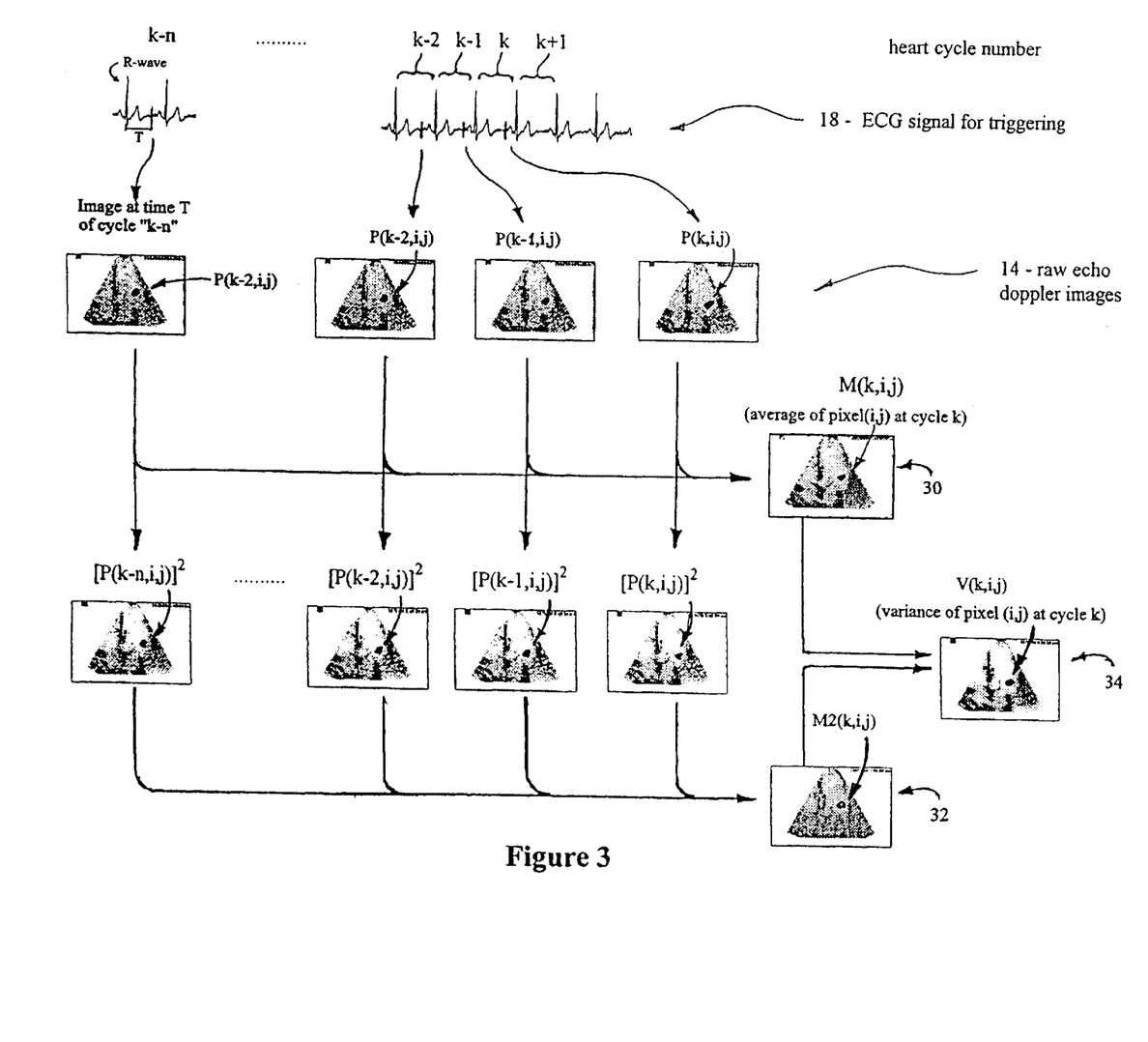
FIG. 3 describes the algorithm to assess the mechanical variability of the heart, or to enhance contrast ultrasound imaging, through gated scanning of the beating heart.
Figure 4A:
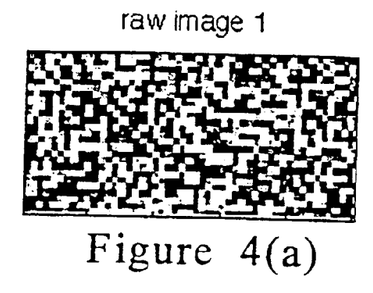
FIGS. 4(a) through 4(d) illustrate a demonstration of variability analysis on synthetic images.
Figure 4B:
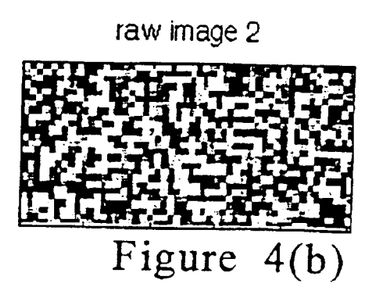
Figure 4C:
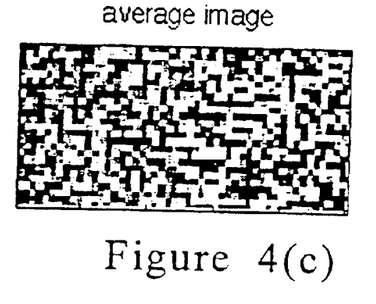
Figure 4D:
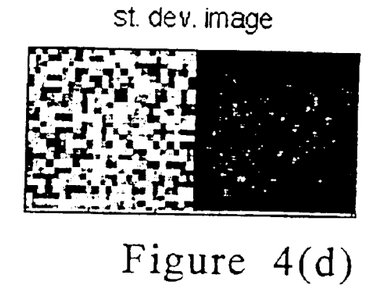

The variability assessment algorithm is schematically presented in FIG. 3. Variability around the mean value can be assessed by various methodologies—e.g. the statistical variance around the statistical mean, or the high-frequency components of the images around the low frequency components. In the following, the approach to assess the statistical variance of the image is presented as the preferred embodiment, however other embodiments may be used to achieve the same kind of information through various filtering schemes.

Referring now to FIG. 3, the acquired image 14 at a specific time T relative to a reference point of the physiologic signal 18 (e.g. the R-wave of the ECG) is denoted as image k. Each pixel (i,j) of the image k is denoted by P(k,i,j). A calculated image is composed of the squared values of each pixel of the raw image ($[P(k,i,j)]^2$).

For real-time application, the mean values of the pixels of images at a specific reference time T are estimated by averaging multiple images at the same reference time but from different physiologic (i.e. cardiac or breathing) cycles. The estimation results are stored as the average image 30 with pixels M(k,i,j). Similarly, the means of the squared-value pixels are estimated by averaging the square-value images at the same reference time T but from different physiologic cycles. The estimation results of the squared variable pixels are stored as the average image 32 with pixels M2(k,i,j). The cardiac cycle is divided into "m" intervals with different images, so there are "m" averaged images and "m" averaged squared-value images. At cycle "k" these averages are recursively calculated by the stored averages from the previous cycle "k−1" and the new raw images of the "k" cardiac cycle:

$$M(k,i,j) = M(k-1,i,j)*(1-\alpha 1) + P(k,i,j)*\alpha 1 \quad\quad 1$$

$$M2(k,i,j) = M2(k-1,i,j)*(1-\alpha 2) + [P(k,i,j)]^2 * \alpha 2 \quad\quad 2$$

where $\alpha 1$ and $\alpha 2$ are parameters which define the memory length of the recursive averaging and their value is between 0 and 1. The new average estimates replace the previous estimates.

For off-line application, these averages can be calculated by summing the pixels of all raw images of "n" different cycles at the same reference time T (thus there is a need to store m*n raw images to enable off-line variability analysis):

$$M(n, i, j) = \left\{ \sum_{k=1}^{n} P(k, i, j) \right\} \Big/ n \quad\quad (3)$$

$$M2(n, i, j) = \left\{ \sum_{k=1}^{n} ([P(k, i, j)]^2) \right\} \Big/ n \quad\quad (4)$$

It is possible to use different memory length for the estimation of the average and the estimation of the variance, which requires the use of different "n" values in equations 3 and 4. For example, while the average estimation may be based on large "n" value, the demonstration of rapid changes (e.g. first pass of contrast agent through the tissue) may require the use of small number of frames (before equilibrium is achieved) for the variance estimation.

The real-time estimation of the variance of the pixels P(k,i,j) at cycle "k", denoted as V(k,i,j), can be derived from the averaged pixels M(k,i,j) and the averaged squared-value pixels M2(k,i,j) (equation (5)). The off-line estimation of the variance is applied, for each time reference, on the stored "n" images by the standard formula for the estimation of the variance (equation (6)):

$$V(k,i,j) = \{M2(k,i,j) - M(k,i,j)*M(k,i,j)\}*k/(k-1) \quad (5)$$

$$V(n, i, j) = \left\{\sum_{k=1}^{n} ([M(k, i, j) - P(k, i, j)]^2)\right\} / (n-1) \quad (6)$$

The resulting pixel variances V(k,i,j) for recursive estimation or V(n,i,j) for off-line estimation form the variance image 34. The same process is applied individually to all "m" images that result from subdividing the cardiac cycle into "m" sequences. The resulting variance images 34 may change during the cardiac cycle and should be interpreted with reference to their relative time T within the cardiac cycle. The variance images 34 are displayed to the user either as additional images or as superimposed (overlay) images.

Referring now to FIG. 4, a demonstration of contrast enhancement by image variability analysis is given by simulated, synthetic images. The top two panels, FIG. 4(*a*) and FIG. 4(*b*), are two out of six synthetic images which are being analyzed. The left half of the image is schematic representation of blood-filled region, and this region is composed of 20% deterministic pattern (i.e. the same pattern of gray level pixels is used in all 6 images) and 80% random pattern (i.e. new patterns are generated for each image). The right half of the image, which represents tissue, is composed of 80% deterministic pattern and 20% random pattern. By comparing the two images, one can hardly distinguish between the patterns in the two halves. The two panels at the bottom are the average image (FIG. 4(*c*)) and the standard deviation image (FIG. 4(*d*)). Each pixel of the average image is the average of the gray levels of the same pixel in the 6 analyzed images, and each pixel of the standard deviation image is the standard deviation of the gray levels of the same pixel in the 6 analyzed images. By looking at the average image one can see the difference between the two portions of the image, however the delineation is much better by the standard deviation image. The same process is applied individually to all "m" images that result from subdividing the physiologic cycle into "m" sequences. The resulting variance images 34 may change during the physiologic cycle and should be interpreted with reference to their relative time T within the physiologic cycle. The variance images 34 are displayed to the user either as additional images or as superimposed (overlay) images.

Figure 5A:
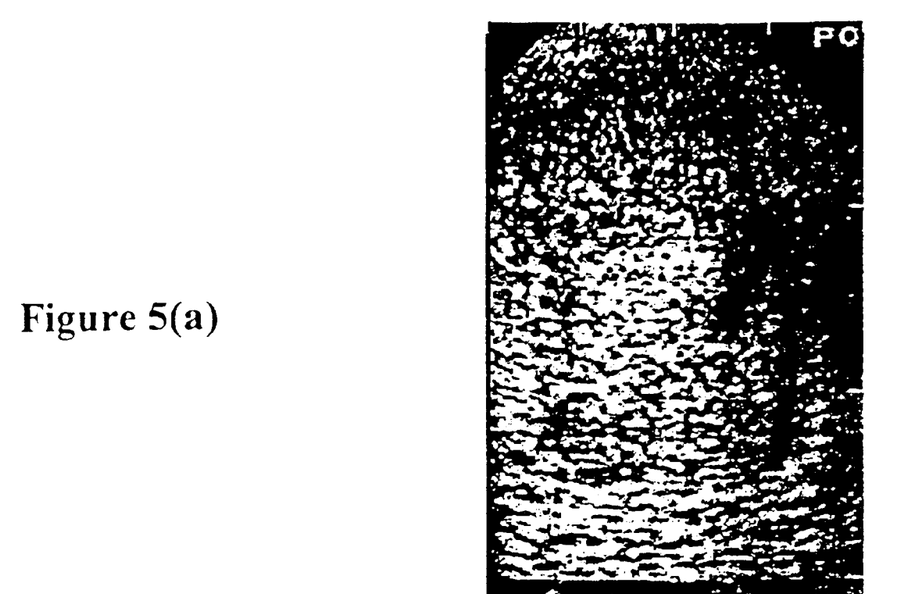
FIGS. 5(a) and 5(b) are example of the enhancement of contrast ultrasound imaging of the heart.
Figure 5B:
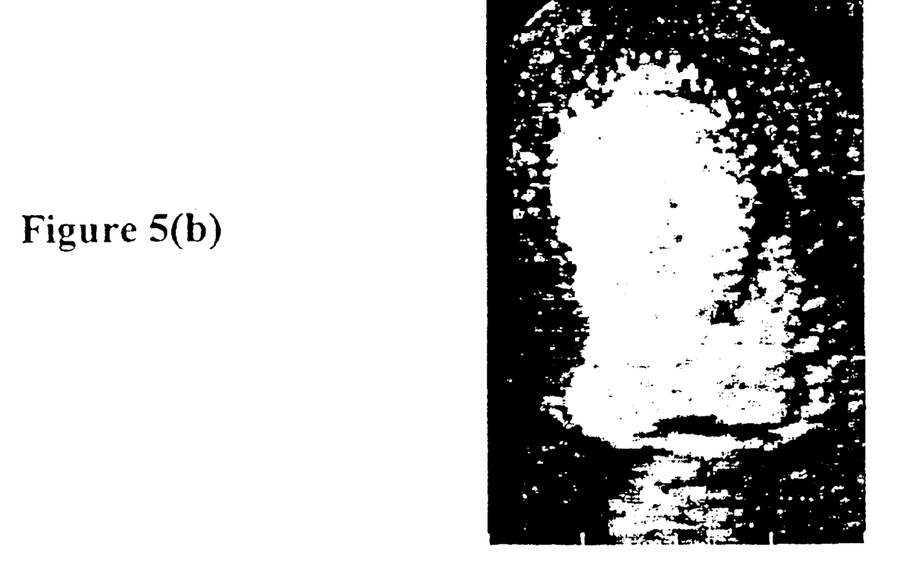

Referring now to FIG. 5, the enhancement of real contrast ultrasound images of the heart is demonstrated. The raw image of the heart with contrast filling of the chamber, FIG. 5(*a*), is significantly enhanced, see FIG. 5(*b*), by the application of the variability analysis. While the region with contrast agent (the left ventricle) becomes brighter, the myocardial regions become darker.

An equivalent approach is used with m-mode and doppler imaging, but the variability analysis is applied on columns of pixels rather than on area (multiple columns) as in 2D image processing. Consequently, each new column of pixels is processed with "n" previous columns which were acquired at the same time T in reference to the reference point of the physiologic signal by analogous approach as described above to the 2D mode.

The user can control the parameters of the recursive or off-line algorithm through user interface 22. Possible controls may include the use of adjustable slide bars (not shown) that can be adjusted to determine the required level of each parameter or through a software interface by using a mouse or other keyboard buttons to change values on a computer screen. Of major importance to the actual application of the invention, as presented herein, are the parameters $\alpha 1$ and $\alpha 2$ which control the memory length of the algorithm, i.e. how many frames are used to estimate the mean and the variance of the images.

The following is a description of one manner of using the system during a routine echo study to display the variability of the mechanical activity of the heart:

The user positions the sensing portion of the ultrasonic scanner 12 in a certain "echo window" which provides the required image of the heart. Initially a slide bar, which determines the value of the parameters $\alpha 1$ and $\alpha 2$, is set to zero, so the processed image is identical to the raw image (no averaging). Once the user is satisfied with the position of the transducer and the acquired images, the user slides the bar to gradually increase the number of the averaged images. The longer the period of time where the transducer is held in a fixed position and the scanned subject does not move, more images are averaged and the quality of the mean and variance estimations improves. However, since other factors which may affect the variance (e.g. breathing, patient's movement or scanner movement) may interfere with the estimation of the true cardiac-related variability, there is an optimal length of acquisition which should be used. Breath hold for 10–20 seconds, which can be achieved with most patients, enables the averaging of 8–20 cardiac cycles and is sufficient to get acceptable estimations of the mean and the variance of the cardiac activity images. If the gating is on both the heart cycle and breathing cycle, longer scans can be averaged until a satisfactory image is obtained.

It will thus be seen that the illustrated apparatus and method can be used for the assessment of the mechanical variability of the heart, as measured through echo-Doppler imaging of the heart. The present invention may add important information about the pathophysiologic status of the myocardial muscle. For example, various disease states or injuries which affect either the whole heart or a region of it may result in either increase or decrease of the variability of the myocardial mechanical performance, compared with the healthy heart.

The following is a description of one manner of using the system during a contrast echo study:

The user positions the sensing portion of the ultrasonic scanner 12 in a certain "echo window" which provides the required image of the scanned structure (e.g. the heart). Initially, a slide bar, which determines the value of the parameters $\alpha 1$ and $\alpha 2$, is set to zero, so the processed image is identical to the raw image (no averaging). Once the user is satisfied with the position of the transducer and the acquired images, the user slides the bar to gradually increase the number of the averaged images. The contrast agent is injected either as a bolus or as continuous drip into a peripheral vein. Following a short delay, the contrast agent appears in the right heart (i.e. the right atrium and the right ventricle) and then cross the pulmonary vascular bed and appears in the left heart. The contrast sequentially enhances the blood pools of the heart, i.e. the right atrium, the right ventricle, the left atrium and the left ventricle. With real-time processing, the enhanced image can be either recorded on a video recorder or saved into digital memory, for later analysis of chamber shape, volumes, and wall motion analysis. From the left ventricle the contrast agent flow with the blood into various organs, including the myocardium. Real-time display of the level of variability with color-coded schemes provides the user with immediate quantitative description of blood perfusion into the myocardiunm (or a non-cardiac tissue) during different phases of the cardiac cycle.

It will also thus be seen that the illustrated apparatus and method can be used for the enhancement of contrast ultrasound imaging. When serial images are analysed, the appearance and wash-out of the contrast result in high level of image variability which can be used to quantify blood flow to various organs and tissues. Furthermore, due to the random nature of the micro-bubbles which are for med by the contrast agent, the variability image can enhance the contrast effect during equilibrium state and to better distinguish between well perfused and low perfused regions and between normal and abnormal (e.g. tumor) tissue.

The apparatus is simple to use and the operation of the method as a real-time implementation does not require significantly more time than is currently required to get a high quality image for measurements and analysis. For enhancement of echo contrast images the invention provides a significant improvement compared with current methodologies like acoustic densitometry, which tracks brightness changes in a small region of interest during single phase of the cardiac cycle (i.e. during triggered scanning), or subtraction of pre-contrast and full-contrast averaged images. The invention can be also applied during exercise and pharmacologic stress test, where it may provide a more sensitive way than currently available methods to detect the appearance of myocardial ischemia.

While a particular system has been described above in conjunction with the Figures for generating a variance image, the invention is not limited to the specific system disclosed and other systems performing these functions are within the contemplation of the invention. Thus, while the invention has been particularly shown and described above with reference to a preferred embodiment, the foregoing and other changes in form and detail may be made therein by one skilled in the art while still remaining within the spirit and scope of the invention.

What is claimed is:

1. A system for assessment of mechanical variability of the heart, comprising:
   a processing unit for receiving and storing scanned ultrasonic images, physiologic signals and a user-control input;
   ultrasonic means for providing said scanned ultrasonic images of the heart of a subject to said unit;
   a physiologic sensor for providing said physiologic signal of the subject for gating said scanned ultrasonic images so that said images are tagged by a specific time within the cardiac cycle with reference to a physiologic reference point when they are received by said unit;
   user means for providing said user-input for processing said gated ultrasonic image to achieve estimation of said variability of the mechanical activity of the heart; and
   display means coupled to said processing unit for receiving and displaying said variability of the mechanical activity of the heart.

2. The system according to claim 1, wherein multiple scanned ultrasound images and physiological signals are processed by two algorithms—one to achieve the average of said images or to follow slow changes of said images; and a second algorithm to achieve the variability of said images as the images variance or as the rapid changes of the images.

3. The system according to claim 1, wherein said variability is derived from the mean value of the images at a specific reference time and the mean of the squared value images at the same reference time.

4. The system according to claim 1, wherein said physiologic signal is provided to said ultrasonic means to initiate a new scan.

5. The system according to claim 1, wherein said variability is determined by a batch algorithm for off-line analysis.

6. The system according to claim 1, wherein said variance image is superimposed over the averaged images in the form of a color-coded overlay.

7. The system according to claim 1, wherein said variance image is superimposed over the averaged images in the form of a contour plot.

8. The system according to claim 1, wherein said ultrasonic means is a two dimensional mode imaging system.

9. The system according to claim 1, wherein said ultrasonic means is an m-mode or Doppler imaging system wherein columns of pixels are processed with previous columns of pixels at the same reference point of the physiologic signal.

10. The system according to claim 1, wherein said variability is obtained according to the following recursive algorithm:

$$V(k,i,j) = \{M2(k,i,j) - M(k,i,j)*M(k,i,j)\}*k/k-1$$

wherein $$M2(k,i,j) = M2(k-1,i,j)*(1-\alpha 2) + [P(k,i,j)]*\alpha 2$$

$$M(k,i,j) = M(k-1,i,j)*(1-\alpha 1) + P(k,i,j)*\alpha 1$$

where M(k,i,j) is the recursive estimate of the mean of the images at the same reference time, M2(k,i,j) is the recursive estimate of the mean of the squared value images at the same reference time, $\alpha 1$ and $\alpha 2$ are parameter lengths that define the memory length of the recursive estimation, i and j index the pixel locations in the image, k indexes the physiologic cycle, P(k,i,j) is the raw scanned image of cycle k at the reference time, and V(k,i,j) is the estimate of the variance image at the reference time.

11. A method of evaluating the variability of the mechanical activity of the heart comprising the steps of:
   detecting an ultrasonic image of the cardiac structure to be displayed;
   gating said ultrasonic image with a physiologic signal so that each image is tagged with a specific time in cycle with reference to a physiological reference point;
   processing images having the same time tag from several cardiac cycles to yield an estimation of the average image and of the variability of the images around said average;
   said gating and said processing being performed on "m" different images that are acquired during a complete cycle of said physiologic signal, and are repeated with images of multiple cardiac cycles; and displaying the resulting "m" averaged images and "m" variability images in their tagged times with reference to said physiologic reference point.

12. The method according to claim 11, wherein said variability is obtained according to the following recursive algorithm:

$$V(k,i,j)=\{M2(k,i,j)-M(k,i,j)*M(k,i,j)\}*k/k-1$$

wherein $$M2(k,i,j)=M2(k-1,i,j)*(1-\alpha 2)+[P(k,i,j)]*\alpha 2$$
$$M(k,i,j)=M(k-1,i,j)*(1-\alpha 1)+P(k,i,j)*\alpha 1$$

where M(k,i,j) is the recursive estimate of the mean of the images at the same reference time, M2(k,i,j) is the recursive estimate of the mean of the squared value images at the same reference time, α1 and α2 are parameter lengths that define the memory length of the recursive estimation, i and j index the pixel locations in the image, k indexes the physiologic cycle, P(k,i,j) is the raw scanned image of cycle k at the reference time, and V(k,i,j) is the estimate of the variance image at the reference time.

13. The method according to claim 12, wherein said step of displaying comprises displaying said variability image superimposed over the average image using a color coded scheme.

14. The method according to claim 12, wherein said step of displaying comprises displaying said variability image superimposed over the average image using a contour plot.

15. The method according to claim 12, wherein said variability is derived from the mean value of the images at a specific reference time and the mean of the squared value images at the same reference time.

16. The method according to claim 12, wherein said physiologic signal is provided to said ultrasonic means to initiate a new scan.

17. The method according to claim 12, wherein said variability is determined by a batch algorithm for off-line analysis.

18. The method according to claim 12, wherein said variance image is superimposed over the averaged images in the form of a contour plot.

19. The method according to claim 12, wherein said ultrasonic means is a two dimensional mode imaging system.

20. The method according to claim 12, wherein said ultrasonic means is an m-mode or Doppler imaging system wherein columns of pixels are processed with previous columns of pixels at the same reference point of the physiologic signal.

21. A system for enhancing contrast ultrasound imaging by variability analysis, comprising:
a processing unit for receiving and storing scanned ultrasonic images, physiologic signals and a user-control input;
ultrasonic means for providing said scanned ultrasonic images of structures injected with contrast agents of a subject to said unit;
a physiologic sensor for providing said physiologic signal of the subject for gating said scanned ultrasonic images so that said images are tagged by a specific time within the cardiac cycle with reference to a physiologic reference point when they are received by said unit;
user means for providing said user-input for processing said gated ultrasonic image; and
display means coupled to said processing unit for receiving and displaying said variability of the scanned structure.

22. The system according to claim 21, wherein multiple scanned ultrasound images and physiological signals are processed by two algorithms—one to achieve the average of said images or to follow slow changes of said images; and a second algorithm to achieve the variability of said images as the images variance or as the rapid changes of the images.

23. The system according to claim 21, wherein said variability is derived from the mean value of the images at a specific reference time and the mean of the squared value images at the same reference time.

24. The system according to claim 21, wherein said physiologic signal is provided to said ultrasonic means to initiate a new scan.

25. The system according to claim 21, wherein said variability is determined by a batch algorithm for off-line analysis.

26. The system according to claim 21, wherein said variance image is superimposed over the averaged images in the form of color-coded overlay.

27. The system according to claim 21, wherein said variance image is superimposed over the averaged images in the form of a contour plot.

28. The system according to claim 21, wherein said ultrasonic means is a two dimensional mode imaging system.

29. The system according to claim 21, wherein said ultrasonic means is an m-mode or Doppler imaging system wherein columns of pixels are processed with previous columns of pixels at the same reference point of the physiologic signal.

30. The system according to claim 21, wherein said variability is obtained according to the following recursive algorithm:

$$V(k,i,j)=\{M2(k,i,j)-M(k,i,j)*M(k,i,j)\}*k/k-1$$

wherein $$M2(k,i,j)=M2(k-1,i,j)*(1-\alpha 2)+[P(k,i,j)]*\alpha 2$$
$$M(k,i,j)=M(k-1,i,j)*(1-\alpha 1)+P(k,i,j)*\alpha 1$$

where M(k,i,j) is the recursive estimate of the mean of the images at the same reference time, M2(k,i,j) is the recursive estimate of the mean of the squared value images at the same reference time, α1 and α2 are parameter lengths that define the memory length of the recursive estimation, i and j index the pixel locations in the image, k indexes the physiologic cycle, P(k,i,j) is the raw scanned image of cycle k at the reference time, and V(k,i,j) is the estimate of the variance image at the reference time.

31. A method of enhancing ultrasound contrast imaging comprising the steps of:
injecting a contrast agent into a vein;
detecting an ultrasonic image of the structure to be displayed;
gating said ultrasonic image with a physiologic signal so that each image is tagged with a specific time in cycle with reference to a physiological reference point;
processing images having the same time tag from several cardiac cycles to yield an estimation of the average image and of the variability of the images around said average;
said gating and said processing being performed on "m" different images that are acquired during a complete cycle of said physiologic signal, and are repeated with images of multiple cardiac cycles; and
displaying the resulting "m" averaged images and "m" variability images in their tagged times with reference to said physiologic reference point.

32. The method according to claim 31, wherein said variability is obtained according to the following formula:

$$V(k,i,j) = \{M2(k,i,j) - M(k,i,j)*M(k,i,j)\}*k/k-1$$

wherein $$M2(k,i,j) = M2(k-1,i,j)*(1-\alpha 2) + [P(k,i,j)]*\alpha 2$$

$$M(k,i,j) = M(k-1,i,j)*(1-\alpha 1) + P(k,i,j)*\alpha 1$$

where M(k,i,j) is the recursive estimate of the mean of the images at the same reference time, M2(k,i,j) is the recursive estimate of the mean of the squared value images at the same reference time, $\alpha 1$ and $\alpha 2$ are parameter lengths that define the memory length of the recursive estimation, i and j index the pixel locations in the image, k indexes the physiologic cycle, P(k,i,j) is the raw scanned image of cycle k at the reference time, and V(k,i,j) is the estimate of the variance image at the reference time.

33. The method according to claim 32, wherein said step of displaying comprises displaying said variability image superimposed over the average image using a color coded scheme.

34. The method according to claim 32, wherein said step of displaying comprises displaying said variability image superimposed over the average image using a contour plot.

35. The method according to claim 32, wherein said variability is derived from the mean value of the images at a specific reference time and the mean of the squared value images at the same reference time.

36. The method according to claim 32, wherein said physiologic signal is provided to said ultrasonic means to initiate a new scan.

37. The method according to claim 32, wherein said variability is determined by a batch algorithm for off-line analysis.

38. The method according to claim 32, wherein said variance image is superimposed over the averaged images in the form of a contour plot.

39. The method according to claim 32, wherein said ultrasonic means is a two dimensional mode imaging system.

40. The method according to claim 32, wherein said ultrasonic means is an m-mode or Doppler imagine system wherein columns of pixels are processed with previous columns of pixels at the same reference point of the physiologic signal.

* * * * *